United States Patent [19]

Fessler et al.

[11] 4,028,401

[45] June 7, 1977

[54] (SUBSTITUTED)UREIDOACETOHYDROX-AMIC ACIDS

[75] Inventors: Dyral C. Fessler; George A. Heavner, both of Norwich; Thomas H. Massey, Sherburne, all of N.Y.

[73] Assignee: Morton-Norwich Products, Inc., Norwich, N.Y.

[22] Filed: July 1, 1976

[21] Appl. No.: 701,658

[52] U.S. Cl. .................... 260/500.5 H; 260/453 R; 260/534 R

[51] Int. Cl.² ..................................... C07C 119/00

[58] Field of Search ............................ 260/500.5 H

[56] References Cited

UNITED STATES PATENTS

| 3,170,953 | 2/1965 | Lashua | 260/500.5 H |
|---|---|---|---|
| 3,465,024 | 9/1969 | Bronstein et al. | 260/500.5 H |
| 3,644,491 | 2/1972 | Adams | 260/500.5 H |

*Primary Examiner*—Joseph E. Evans
*Attorney, Agent, or Firm*—Anthony J. Franze

[57] ABSTRACT

A series of (substituted)ureidoacetohydroxamic acids are useful as inhibitors of Angiotensin I converting enzyme.

9 Claims, No Drawings

(SUBSTITUTED)UREIDOACETOHYDROXAMIC ACIDS

This invention is concerned with chemical compounds and particularly with (substituted-)ureidoacetohydroxamic acids of the formula:

wherein R is isobutyl, hydrogen, methyl, benzyl, 4-aminobutyl or hexyl and $R_1$ is hydrogen or benzyl.

The members of this series are potent inhibitors of the enzyme responsible for the conversion of Angiotensin I to the powerful pressor agent Angiotensin II associated with hypertension. They are thus capable of interrupting the biological pathway leading to the formation of that active pressor substance. For example, they inhibit the pure converting enzyme isolated from rabbit lung tissue at levels of from 0.4 to $3.2 \times 10^{-5}$ moles per liter.

The methods currently preferred for the preparation of the compounds of this invention are shown by the following examples:

EXAMPLE I

N-[$N^1$-($N^2$-Hydroxycarbamoylmethyl)carbamoyl]-DL-leucine

A. t-Butyloxycarbonyl-O-Benzyl Glycine Hydroxamic Acid

O-Benzylhydroxylamine hydrochloride (15.0 g, 93.8 mMol) was dissolved in methanol (150 ml) and added to a solution of potassium hydroxide (5.27 g, 93.8 mMol) in methanol (50 ml). The resulting mixture was cooled, filtered, evaporated, dissolved in tetrahydrofuran (25 ml) and filtered as solution A. t-Butyloxycarbonyl glycine (16.4 g, 93.8 mMol) was dissolved in tetrahydrofuran (75 ml), triethylamine (13.2 ml, 93.8 mMol) added and the solution cooled to $-10°$ C. with dry ice/ethanol. Iso-butyl chloroformate (12.2 ml, 93.8 mMol) was added and the solution stirred cold 2 minutes, before adding solution A dropwise. The mixture was stirred cold 1 hour and at room temperature 2 hours, filtered, evaporated, dissolved in ethyl acetate (100 ml), washed with water (3 × 50 ml), dried over magnesium sulfate and evaporated to an oil.

B. O-Benzyl Glycine Hydroxamic Acid Trifluoroacetate t-Butyloxycarbonyl-O-benzyl glycine hydroxamic acid [(17.5 g, 62.5 mMol) see Step A] was dissolved in trifluoroacetic acid (25 ml), stirred at room temperature 30 minutes, and ether (200 ml) added. The product was filtered and dried to yield: 9.0 g, m.p. 122°–124°.

Anal. Calc'd. for $C_{11}H_{13}F_3N_2O_4$: C, 44.90; H, 4.45; N, 9.52. Found: C, 44.56; H, 4.57; N, 9.52.

C. Benzyl-N-[$N^1$-($N^2$-Benzyloxycarbamoylmethyl)Carbamoyl]DL-Leucinate

Methyl-L-leucinate hydrochloride (3.63 g, 0.02 m) was suspended in toluene (75 ml) and heated to 130° C while bubbling nitrogen through the solution. Phosgene was bubbled into the 130° C solution for 30 minutes. The solution was allowed to cool to room temperature while flushing with nitrogen, and evaporated to an oil. A solution of O-benzyl glycine hydroxamic acid trifluoroacetate (5.9 g, .02 m) in pyridine (50 ml) was added to the oil and allowed to set at room temperature overnight. The solution was evaporated to an oil, dissolved in ethyl acetate (50 ml), washed with water (3 × 25 ml), dried over magnesium sulfate, evaporated to an oil and crystallized from ethyl acetate/pet. ether. The product was recrystallized from ethyl acetate/1:1 ether:pet. ether to yield: 4.0 g, m.p. 100°–102°.

Anal. Calc'd. for $C_{17}H_{25}N_3O_5$: C, 58.10; H, 7.17; N, 11.96. Found: C, 58.24; H, 7.34; N, 11.95.

D. N-[$N^1$($N^2$-Hydroxycarbamoylmethyl)carbamoyl]-DL-Leucine

Benzyl-N-[$N^1$-($N^2$-Benzyloxycarbamoylmethyl)carbamoyl]-DL-leucinate (3.45 g, 9.8 mMol) was dissolved in methanol (25 ml), 10% Pd/C catalyst (0.5 g) added, and the mixture stirred in a hydrogen atmosphere about 6 hours. The mixture was filtered, an equal volume of 1N sodium hydroxide (40 ml) added, and the solution stirred at room temperature 1 hour. The methanol was evaporated and the resulting solution was chromatographed on a 20 gram CG-120 (H$^+$) column. Fractions containing product were lyophilized to yield: 1.0 g, m.p. 80°–87° (dec).

Anal. Calc'd. for $C_9H_{17}N_3O_5$: C, 43.72; H, 6.93; N, 17.00. Found: C, 43.98; H, 7.15; N, 16.52.

EXAMPLE II

N,N'-Carbonyl-glycine-glycine Hydroxamic Acid Monohydrate

A. Ethyl glycinate hydrochloride (2.8 g, .02 m) was suspended in toluene (75 ml) and heated to 120° C while bubbling nitrogen through the solution. Phosgene was bubbled into the 120° C solution for 2 hours. The solution was allowed to cool to room temperature while flushing with nitrogen, and evaporated to an oil. A solution of O-benzyl glycine hydroxamic acid trifluoroacetate (5.9 g, 0.02 m) in pyridine (50 ml) was added to the oil and allowed to set at room temperature overnight. The solution was evaporated to an oil, dissolved in ethyl acetate (50 ml), washed with water (3 × 25 ml), dried over magnesium sulfate, evaporated to an oil and crystallized from ethyl acetate to yield: 2.8 g, m.p. 128° C.

Anal. Calc'd. for $C_{14}H_{19}N_3O_5$: C, 54.54; H, 5.88; N, 13.63. Found: C, 54.21; H, 6.27; N, 13.62.

B. The product of A. was dissolved in methanol (25 ml), 10% Pd/C catalyst (0.5 g) added, and the mixture stirred in a hydrogen atmosphere about 4 hours. The mixture was filtered, an equal volume of 1N sodium hydroxide (40 ml) added, and the solution stirred at room temperature 1 hour. The methanol was evaporated and the aqueous residue chromatographed on a 20 gram CG-120 (H$^+$) column. Fractions containing product were combined, lyophilized and crystallized from nitromethane, using a minimum of methanol/ether to yield: 1.0 g, m.p. 140° (dec).

Anal. Calc'd. for $C_5H_9N_3O_5H_2O$: C, 28.71; H, 5.30; N, 20.09; $H_2O$, 8.6%. Found: C, 28.86; H, 5.32; N, 19.55; $H_2O$, 8.7%.

EXAMPLE III

N,N'-Carbonyl-DL-alanine-glycine Hydroxamic Acid Hemihydrate

A. Ethyl L-alanate hydrochloride (3.07 g, .02 m) was suspended in toluene (75 ml) and heated to 125° C while bubbling nitrogen through the solution. Phosgene was bubbled into the 125° C solution for 30 minutes. The solution was allowed to cool to room temperature while flushing with nitrogen, and evaporated to an oil. A solution of O-benzyl glycine hydroxamic acid trifluoroacetate (5.9 g, .02 m) in pyridine (50 ml) was added to the oil and allowed to set at room temperature overnight. The solution was evaporated to an oil, dissolved in ethyl acetate (50 ml), washed with water (3 × 25 ml), dried over magnesium sulfate, evaporated to an oil and crystallized from ethyl acetate to yield: 2.1 g, m.p. 99°–100°.

Anal. Calc'd. for $C_{15}H_{21}N_3O_5$: C, 55.72; H, 6.55; N, 13.00. Found: C, 55.23; H, 6.47; N, 13.01.

B. The compound of A. (2.1 g, 6.5 mMol) was dissolved in methanol (25 ml), 10% Pd/C catalyst (0.5 g) added, and the mixture stirred in a hydrogen atmosphere about 3 hours. The mixture was filtered, an equal volume of 1N sodium hydroxide (50 ml) added, and the solution stirred at room temperature 1 hour. The methanol was evaporated and the aqueous residue chromatographed on a 20 gram CG-120 ($H^+$) column. Fractions containing product were lyophilized to yield: 0.9 g, m.p. 110° (dec).

Anal. Calc'd. for $C_6H_{11}N_3O_5 \cdot \frac{1}{2} H_2O$: C, 33.64; H, 5.65; N, 19.62; $H_2O$, 4.2%. Found: C, 34.06; H, 5.93; N, 19.32; $H_2O$, 4.0%.

EXAMPLE IV

N,N'-Carbonyl-DL-phenylalanine-glycine Hydroxamic Acid

A. Methyl-DL-phenylalanate hydrochloride (4.3 g, 0.02 m) was suspended in toluene (75 ml) and heated to 125° C while bubbling nitrogen through the solution. Phosgene was bubbled into the 125° C solution for 30 minutes. The solution was allowed to cool to room temperature while flushing with nitrogen, and evaporated to an oil. A solution of O-benzyl glycine hydroxamic acid trifluoroacetate (5.9 g, 0.02 m) in pyridine (50 ml) was added to the oil and allowed to set at room temperature overnight. The solution was evaporated to an oil, dissolved in ethyl acetate (50 ml), washed with water (3 × 25 ml), dried over magnesium sulfate, evaporated to an oil and crystallized twice from ethyl acetate to yield: 4.1 g, m.p. 90°.

Anal. Calc'd. for $C_{20}H_{23}N_3O_5$: C, 62.32; H, 6.02; N, 10.90. Found: C, 61.94; H, 5.95; N, 10.67.

B. The compound of A. (5.3 g, 13.8 mMol) was dissolved in methanol (50 ml), 10% Pd/C catalyst (1.0 g) added, and the mixture stirred in a hydrogen atmosphere about 3 hours. The mixture was filtered, an equal volume of 1N sodium hydroxide (50 ml) added, and the solution stirred at room temperature 1 hour. The methanol was evaporated and the aqueous residue chromatographed on a 40 gram CG-120 ($H^+$) column. Fractions containing product were lyophilized to yield: 3.2 g, m.p. 74°–90° (dec).

Anal. Calc'd. for $C_{12}H_{15}N_3O_5$: C, 51.24; H, 5.38; N, 14.94. Found: C, 51.38; H, 6.32; N, 14.11.

EXAMPLE V

N,N'-Carbonyl-L-alanine glycine hydroxamic acid

A. N,N'-Carbonyl-L-alanine benzyl ester glycine hydroxamic acid benzyl ester 1,1-Carbonyl diimidazole (12.96 g, 0.08 moles) was dissolved in 200 ml of dry dimethylformamide. To this was added dropwise over a period of 0.5 hr a solution of 28.08 g (0.08 moles) of L-alanine benzyl ester p-toluene sulfonate and 8.08 g (0.08 moles) of triethyl amine in 200 ml of dry dimethylformamide. The resulting solution was stirred for 1 hr at room temperature. To this solution was added dropwise over a period of 0.5 hr 23.52 g (0.08 moles) of glycine hydroxamic acid benzyl ester trifluoroacetate in 200 ml of dry pyridine. The resulting solution was stirred for 1.5 hr at room temperature. The solvent was evaporated under reduced pressure and the residue triturated twice with 200 ml of cold water. The resulting solid was dried and crystallized from absolute ethanol to give 19 g, m.p. 125.5°–127.5°.

Anal. Calc'd. for $C_{20}H_{23}N_3O_5$: C, 62.32; H, 6.02; N, 10.90. Found: C, 62.11; H, 6.01; N, 10.76.

B. N,N'-Carbonyl-L-alanine glycine hydroxamic acid

N,N'-Carbonyl-L-alanine benzyl ester glycine hydroxamic acid benzyl ester (16.0 g, 41.6 mMol) and 4 g of 10% Pd/C were suspended in 500 ml of anhydrous methanol and stirred under a positive pressure of hydrogen. Hydrogen uptake ceased after 2400 ml (uncorr). The solution was filtered and evaporated. The residue was crystallized from methanol/nitromethane to give 4.8 g, m.p. 152.5°–154°; $[\alpha]_D^{23.5°}$ − 22.6° (C=1.00, $H_2O$). A second crop of 2.8 g precipitated.

Anal. Calc'd. for $C_6H_{11}N_3O_5$: C, 35.12; H, 5.40; N, 20.48. Found: C, 35.36; H, 5.54; N, 20.35.

EXAMPLE VI

N,N'-Carbonyl-L-Lysine Glycine hydroxamic acid

A. N,N'-Carbonyl-ε-Z-L-Lysine benzyl ester-Glycine hydroxamic acid benzyl ester 1,1'-Carbonyldiimidazole (6.48 g, 0.04 moles) was dissolved in 100 ml of dry dimethylformamide. ε-Z-L-Lysine benzyl ester toluene sulfonic acid salt (21.06 g, 0.04 moles) and triethylamine (4.04 g, 0.04 moles) were dissolved in 100 ml of dry dimethylformamide and added to the first solution with vigorous stirring over a period of 0.5 hr. The resulting solution was stirred for 1.0 hr at room temperature. Glycine hydroxamic acid benzyl ester trifluoroacetate (11.76 g, 0.04 moles) was dissolved in 100 ml of dry pyridine and added to the dimethylformamide solution over a period of 15 minutes. The solution was stirred for 1.5 hr at room temperature.

The solvent was evaporated under reduced pressure and the residue triturated with 2 × 300 ml of water. The resulting white solid was collected by filtration, washed well with water and dried to give 19.56 g. The solid was recrystallized from ethyl acetate to give 12.8 g of a white solid, m.p. 133°–5°. A second crop of 2.05 g was obtained, m.p. 126°–30°.

Anal. Calc'd. for $C_{33}H_{36}N_4O_7$: C, 64.57; H, 6.29; N, 9.72. Found: C, 64.52; H, 6.38; N, 9.67.

B. N,N'-Carbonyl-L-Lysine-Glycine hydroxamic acid

N,N'-Carbonyl-ε-Z-L-Lysine benzyl ester-Glycine hydroxamic acid benzyl ester (5.76 g, 0.01 mole) and 10% Pd/C (1.5 g) were suspended in 150 ml of anhydrous methanol and stirred under a positive pressure of hydrogen. Measured volume change of gas was 750 mls (uncorr.). The solids were removed by filtration and washed with methanol. The filter cake was then washed with water and the aqueous wash collected. Ethanol was added to the aqueous wash until the solution became cloudy and the solution was cooled. The solid was collected by filtration, washed with ethanol and dried to give 1.9 g, m.p. 196° (dec), $[\alpha]_{589}^{25.0°} = +10.14$, $[Hg]_{365}^{25.0°} = +34.84$ [$c = 1.016$, $H_2O$].

Anal. Calc'd. for $C_9H_{18}N_4O_5$: C, 41.21; H, 6.92; N, 21.37. Found: C, 40.96; H, 6.89; N, 21.19.

EXAMPLE VII

N,N'-Carbonyl-DL-α-Aminocaprylic Acid Glycine Hydroxamic Acid

A. DL-α-aminocaprylic acid benzyl ester p-toluene sulfonic acid salt

DL-α-Aminocaprylic acid (39.75 g, 0.25 moles), p-toluene sulfonic acid monohydrate (48.5 g, 0.255 moles), benzyl alcohol (100 mls) and benzene (50 mls) were heated under reflux in a 1 liter round bottom flask equipped with a Dean-Stark trap and a condenser. After 4 hours the solution was cooled and 250 ml of benzene and 1800 ml of ether added. The solid was collected by filtration and then dissolved in 750 ml of chloroform. The chloroform solution was washed with 4 × 500 ml of 10% $NaHCO_3$, 4 × 500 ml of 0.5M NaOH and 4 × 500 ml water and dried ($MgSO_4$). The drying agent was removed by filtration and the solvent evaporated to give 36 g of an oil. To secure a crystal form p-toluene sulfonic acid monohydrate (28.3 g, 0.15 moles), 50 ml benzene and 5 ml ethanol were heated under reflux and water removed with a Dean-Stark trap. The solution was added to a solution of the oil in 50 ml of benzene and then to the combined benzene solution was added 350 ml of hexane. The solution was cooled and the resulting solid collected by filtration and dried to give 43 g, m.p. 114°–117°.

Anal. Calc'd. for $C_{22}H_{31}NO_5S$: C, 62.98; H, 6.97; N, 3.34. Found: C, 62.71; H, 7.39; N, 3.37.

B. N,N'-Carbonyl-DL-α-aminocaprylic acid benzyl ester-Glycine hydroxamic acid benzyl ester 1,1'-Carbonyldiimidazole (6.48 g, 0.04 moles) was dissolved in 100 ml of dry dimethylformamide. DL-α-aminocaprylic acid benzyl ester p-toluene sulfonic acid salt (16.86 g, 0.04 moles) and triethyl amine (4.04 g, 0.04 moles) were dissolved in 100 ml of dry dimethylformamide and added to the first solution with vigorous stirring over a period of 0.5 hr. The resulting solution was stirred for 1.5 hr at room temperature. Glycine hydroxamic acid benzyl ester trifluoroacetic acid salt (11.76 g, 0.04 moles) was dissolved in 100 ml of dry pyridine and added to the dimethylformamide solution over a period of 0.5 hr. Stirring was continued for 2 hr. The solvent was evaporated under reduced pressure and the residue triturated with 500 ml water. The solid was collected by filtration, washed with water and dried to give 16 g. The material was recrystallized from 100 ml of ethanol to give 11.3 g of a white solid, m.p. 117°–120°.

Anal. Calc'd. for $C_{25}H_{31}N_3O_5$: C, 65.91; H, 7.30; N, 9.22. Found: C, 65.73; H, 7.13; N, 9.18.

C. N,N'-Carbonyl-DL-α-aminocaprylic acid-Glycine hydroxamic acid

N,N'-Carbonyl-DL-α-aminocaprylic acid benzyl ester-glycine hydroxamic acid benzyl ester (10.0 g, 0.0219 mole) and 1.5 g of 10% Pd/C were suspended in 200 ml of absolute methanol and stirred under a positive pressure of hydrogen (uptake: 1090 ml, uncorr.). The catalyst was removed by filtration and the filtrate evaporated under reduced pressure. The resulting solid was crystallized from 100 ml water and 25 ml methanol to give 5.51 g, m.p. 155°–157.5° dec.

Anal. Calc'd. for $C_{11}H_{21}N_3O_5$: C, 47.99; H, 7.79; N, 15.27. Found: C, 48.07; H, 7.43; N, 15.18.

EXAMPLE VIII

N,N¹-Carbonyl-L-alanine-L-phenylalanine-Hydroxamic acid

A. N,N¹-Carbonyl-L-alanine benzyl ester-L-phenylalanine-hydroxamic acid benzyl ester 1,1'-Carbonyldiimidazole (6.49 g, 40 mMol) was dissolved in 100 ml of dry dimethylformamide. To this was added, dropwise over a period of 0.5 hr with rapid stirring, a solution of L-alanine benzyl ester TsOH (14.06 g, 40 mMol) and triethylamine (4.04 g, 40 mMol) dissolved in 100 ml of dry dimethylformamide. The resulting solution was stirred for 1 hr at room temperature. To this solution was added, dropwise over a period of 15 min, a solution of phenylalanine hydroxamic acid benzyl ester trifluoroacetate (15.37 g, 40 mMol) in 100 ml of dry pyridine. The resulting solution was stirred for 2 hr at room temperature. The solvent was removed under reduced pressure and the resulting oil was triturated with 500 ml cold $H_2O$ (twice). The resulting solid was dissolved in 200 ml hot ethylacetate and dried over $MgSO_4$ (while hot). The drying agent was removed by filtration and the filtrate was cooled at room temperature then refrigerated overnight. The resulting solid was removed by filtration giving 12 g; m.p. 151°–153°. A second crop of 1.1 g was obtained identical to the first crop.

Anal. Calc'd. for $C_{27}H_{29}N_3O_5$: C, 68.19; H, 6.15; N, 8.84. Found: C, 68.23; H, 6.20; N, 8.85.

B. N,N¹-Carbonyl-L-alanine-L-phenylalanine-Hydroxamic acid Hemihydrate

N,N¹-Carbonyl-L-alanine benzyl ester-L-phenylalanine hydroxamic acid benzyl ester (13 g, 27.3 mMol) and 3 g of 10% Pd/C were suspended in 400 ml anhydrous methanol and stirred under positive pressure of hydrogen. The catalyst was filtered, and the filtrate evaporated under reduced pressure. The resulting residue was dissolved in 100 ml $H_2O$ and lyophilized (twice) to give 7.54 g of a solid, m.p. 82°–124° (dec.-)$[\alpha]_D^{25°} = 7.7°$ [$C = 0.507$; MeOH], $[Hg]_{365}^{25°} = 33.7°$ [$C = 0.507$; MeOH].

Anal. Calc'd. for $C_{13}H_{17}N_3O_5 \cdot \frac{1}{2} H_2O$: C, 52.08; H, 5.88; N, 14.01. Found: C, 52.11; H, 6.13; N, 13.59.

What is claimed is:

1. A compound of the formula:

wherein R is isobutyl, hydrogen, methyl, benzyl, 4-aminobutyl or hexyl and $R_1$ is hydrogen or benzyl.

2. The compound N,[$N^1$-($N^2$-hydroxycarbamoylmethyl)carbamoyl]-DL-leucine.

3. The compound N,N'-carbonyl-glycine-glycine hydroxamic acid.

4. The compound N,N'-carbonyl-DL-alanine-glycine-hydroxamic acid.

5. The compound N,N'-carbonyl-DL-phenylalanine-glycine hydroxamic acid.

6. The compound N,N'-carbonyl-L-alanine-glycine hydroxamic acid.

7. The compound N,N'-carbonyl-L-lysine-glycine hydroxamic acid.

8. The compound N,N'-carbonyl-DL-α-amino-caprylic acid-glycine hydroxamic acid.

9. The compound N,N'-carbonyl-L-alanine-L-phenylalanine-hydroxamic acid.

* * * * *

UNITED STATES PATENT OFFICE
CERTIFICATE OF CORRECTION

Patent No. 4,028,401　　　　　　　　　Dated June 7, 1977

Inventor(s)　Dyral C. Fessler et al.

It is certified that error appears in the above-identified patent and that said Letters Patent are hereby corrected as shown below:

Column 1, line 62, "Benzyl" should read -- Methyl --.

Column 2, line 18, "Benzyl" should read -- Methyl --.

Signed and Sealed this

Eighteenth Day of October 1977

[SEAL]

Attest:

RUTH C. MASON
Attesting Officer

LUTRELLE F. PARKER
Acting Commissioner of Patents and Trademarks